(12) United States Patent
Schadt

(10) Patent No.: US 7,481,124 B2
(45) Date of Patent: Jan. 27, 2009

(54) POSITIVE-DISPLACEMENT SAMPLING APPARATUS

(75) Inventor: John C. Schadt, Watertown, WI (US)

(73) Assignee: Sentry Equipment Corp., Oconomowoc, WI (US)

( * ) Notice: Subject to any disclaimer, the term of this patent is extended or adjusted under 35 U.S.C. 154(b) by 360 days.

(21) Appl. No.: 11/439,585

(22) Filed: May 24, 2006

(65) Prior Publication Data

US 2007/0272038 A1 Nov. 29, 2007

(51) Int. Cl.
*G01N 1/14* (2006.01)

(52) U.S. Cl. .................................................. 73/863.86

(58) Field of Classification Search .. 73/863.81–863.86
See application file for complete search history.

(56) References Cited

U.S. PATENT DOCUMENTS

| | | | | |
|---|---|---|---|---|
| 2,370,260 A | * | 2/1945 | Robison | 73/863.86 X |
| 3,007,340 A | | 11/1961 | Kraftson | 73/866.5 |
| 4,147,062 A | | 4/1979 | Jaeger | 73/863.83 |
| 4,262,533 A | | 4/1981 | Jaeger | 73/863.11 |
| 4,294,124 A | | 10/1981 | Kalwaitis | 73/863.85 |
| 4,475,410 A | | 10/1984 | Jaeger | 73/863.84 |
| 4,537,071 A | | 8/1985 | Waterman | 73/866.5 |
| 4,628,732 A | | 12/1986 | Makinen | 73/866.5 |
| 4,744,255 A | | 5/1988 | Jaeger | 73/863.84 |
| 5,585,576 A | * | 12/1996 | Jaeger | 73/863.85 |
| 5,747,708 A | | 5/1998 | Weiberth | 73/863.81 |
| 5,905,213 A | | 5/1999 | Jaeger | 73/863.85 |
| 6,164,145 A | * | 12/2000 | Jaeger | 73/863.83 |
| 6,792,818 B2 | | 9/2004 | Jaeger | 73/863.86 |
| 6,886,420 B2 | | 5/2005 | Handel | 73/863.85 |

* cited by examiner

*Primary Examiner*—Thomas P Noland
(74) *Attorney, Agent, or Firm*—Jansson Shupe & Munger Ltd.

(57) ABSTRACT

Apparatus for withdrawing a liquid sample from a vessel, the apparatus affixed to the vessel and having (a) a plunger forming a sample-receiving space movable from the vessel interior to and beyond a sample-delivery site, and (b) a valve for closing the vessel when the plunger is beyond the sample-delivery site. In the sampling apparatus, the sample-delivery site is incorporated in the valve.

19 Claims, 10 Drawing Sheets

POSITIVE-DISPLACEMENT SAMPLING APPARATUS

FIELD OF THE INVENTION

This invention is related generally to apparatus for extracting samples of liquid from vessels, and in particular to positive-displacement sampling apparatus with an inline valve.

BACKGROUND OF THE INVENTION

There is a need with many manufacturing operations and processes and within liquid transportation systems to monitor the composition or other properties of the liquid material which is either contained in or flowing within a vessel. Often what is required is to capture a sample of the liquid from within the vessel in order to make the necessary measurements. It is most desirable to be able to capture such samples without interference with or contamination to the processes being monitored. Non-interference with a process is often achieved by ensuring that vessel pressure is maintained throughout the sampling-capturing operation. Further, it is often a requirement that samples be taken at regular and frequent intervals so that reliability, operator safety, and sampler maintenance and longevity are important requirements for such samplers.

A number of samplers which are used in such manufacturing or process applications are devices which capture small, discrete samples of liquid. An example of such a sampler is disclosed in U.S. Pat. No. 6,792,818 by Ben E. Jaeger. This positive-displacement sampler includes a plunger having a sample receiving recess and a connecting device which couples the sampler to a vessel at an aperture in the vessel. The sampler is attached to the connecting device, and the connecting device is moveable between a first position placing the sampler into, and a second position taking the sampler out of communication with the aperture. With the connecting device in the first position, the plunger is reciprocated to extend the plunger and its recess through the connecting device and vessel aperture into product in the vessel to receive a product sample in the recess. The plunger is then retracted from the vessel and through the connecting device to deliver the product sample to a collection point. During reciprocation of the plunger, a liquid seal is maintained between the vessel interior and sample collection point, and when the connecting device is moved to the second position, the sampler can be detached from the connecting device for service or repair, without escape of liquid from the vessel through the connecting device.

Particularly severe requirements exist for samplers used in applications where the liquid being sampled contains a solid phase. An example of this is in the handling of oil sands in which the liquid may contain bituminous sand, oil, hot water, and possibly clay. The solid phase is the source of abrasive material which creates a particularly difficult operational environment for samplers. The abrasive material can become trapped in regions around seals, particularly when elements within the sampler become misaligned due to, for example, frictional forces during movement of sampler elements, thereby allowing the abrasive material to flow by leakage into areas in which it is not intended to be, causing excessive wear. Also, when seals move past entry and exit interfaces within valves and other elements within a sampler, abrasive material can easily cause the seals to wear far too rapidly, necessitating frequent and costly maintenance on the sampler.

The sampler disclosed in U.S. Pat. No. 6,792,818 described above, when applied in applications such as oil sands, operates in a manner in which excessive seal/interface traverses and misalignment are both causes of seal wear. As an example, in the sampling of such abrasive liquids, sampling frequencies may be as high as five samples per hour and may result in seals being replaced as often as once each week, creating an extremely high maintenance cost.

Another desirable and intended feature for samplers is the ability to be able to achieve what is termed "double block and bleed" capability, the ability to isolate the sampler from vessel pressure and to verify that such isolation has indeed taken place so that the sampler can be disconnected. If seals are worn and misalignment causes further leakage, the sampler cannot be relied on to achieve the required isolation. The invention disclosed in the '818 patent can exhibit such unwanted behavior when the ball valve, which is "floating" within a set of seals, becomes misaligned and causes leakage of unwanted vessel pressure, thereby causing a potentially unsafe condition for an operator performing maintenance on the sampler or simply taking a sample in the course of regular vessel monitoring.

U.S. Pat. No. 5,905,213, also by Ben E. Jaeger, discloses a sampler in which the forward end of the sampler housing is coupled to a movable valve for movement with the valve, and the housing and valve have axially-aligned bores. Movement of the valve places the forward end of its bore into and out of communication with an opening in a vessel containing the liquid to be sampled. A plunger in the housing bore has a sample-receiving recess intermediate its ends, and with the forward end of the valve bore placed into communication with the interior of the vessel, the plunger is reciprocated forward in the housing and valve bores to project the recess into the vessel to receive a product sample therein. The plunger is then reciprocated rearward to retract the product sample containing recess from the vessel and through the valve and housing bores to a sample collection point in the housing. When repair or replacement of the sampler is required, the valve is moved to place the forward end of the valve bore out of communication with the vessel interior, whereupon the sampler housing can be disconnected from the valve without outflow of liquid product from the vessel through the valve bore. A disadvantage of the arrangement is that the entirety of the sampler moves conjointly with movement of the valve between its open and closed positions, so a relatively large unobstructed area must be provided around the sampler to accommodate such movement, which limits freedom of location of the sampling apparatus. In addition, to accommodate mounting of the sampler housing on the valve, the valve must be relatively large to accommodate connection of the sampler housing to it, resulting in increased manufacturing costs.

Existing samplers currently used as described above fall short of delivering effective, safe and cost-effective sampling. Thus, there is a need for a sampler which satisfies the objectives as set forth in the following section.

OBJECTS OF THE INVENTION

It is an object of this invention, in the field of process sampling technology, to provide an improved sampler which incorporates the isolation valve within the sampler apparatus.

Another object is to provide a sampler which deposits the liquid sample from a location within the valve of the sampler.

Another object of the present invention is to provide a sampler which can be used with abrasive liquids.

Another object of this invention is to provide a sampler which minimizes wear on seals within the sampler.

Another object of this invention is to provide a sampler which minimizes leakage at the seals within the sampler.

Another object of this invention is to provide a sampler with a valve in which valve core is completely encapsulated by its trunnion supports and, further, in which the valve core and stem are structurally integral.

Another object of this invention is to provide a sampler which reduces the number of times seals traverse across interfaces within the sampler during the sampling process.

A further object of this invention is to provide a sampler which protrudes a reduced length from the vessel and thus also has reduced weight.

It is an object of this invention to provide a sampler with "double-block-and-bleed" capability with a single valve.

It is also an object of this invention to provide a sampler with improved operator safety.

Still another object of the invention is to provide a sample which minimizes misalignment within the valve.

Yet another object of the invention is to provide a sampler with a valve which is less sensitive to any misalignment that may occur within the valve.

These and other objects of the invention will be apparent from the following descriptions and from the drawings.

SUMMARY OF THE INVENTION

The invention is an improvement in apparatus for withdrawing a liquid sample from a vessel. Such apparatus is affixed to the vessel and has (a) a plunger forming a sample-receiving space movable from the vessel interior to and beyond a sample-delivery site and (b) a valve for closing the vessel when the plunger is beyond the sample-delivery site. The improvement of the instant invention comprises the sample-delivery site being incorporated in the valve.

In some preferred embodiments of the invention, the valve is a trunnion valve and the valve has a stem and a central portion, the central portion dividing the stem into a first stem portion and a second stem portion and having a through-hole with an axis substantially perpendicular to the stem axis. In highly preferred embodiments, the first stem portion includes a discharge/bleed port aligned substantially along the axis of the stem for discharge of the sample from the sample-receiving space when such space is at the sample-delivery site. Further, the plunger in some highly preferred embodiments passes through the through-hole to receive a sample from the vessel interior and to deliver the sample to the discharge/port.

In some preferred embodiments, the through-hole in the central portion of the valve is a clearance hole for the plunger, and in some preferred embodiments, the second stem portion includes a purge/flush inlet port.

In highly preferred embodiments of the inventive sampling apparatus, the valve includes first and second valve seats that form stem-engagement surfaces for the first and second stem portions, respectively, and that together form a central-portion-engagement surface. In such embodiments, the first and second valve seats together surround, support and seal the central portion and the first and second stem portions.

In some embodiments, the plunger moves within first and second axially-aligned plunger cylinders, (a) the first on the vessel side of the valve and the second on the opposite side of the valve, (b) the sample-receiving space is an annular space, and (c) the plunger includes first and second plunger seals each mounted beyond a respective end of the sample-receiving space and spaced such that when the sample-receiving space is at the sample-delivery site, the first and second plunger seals are engaging the first and second plunger cylinders, respectively.

In highly preferred embodiments, the valve is a ball valve. In other embodiments, the valve is a plug valve. Further, some embodiments include a compound actuator for plunger movement.

Highly preferred embodiments of the inventive sampling apparatus include a bleed valve to effect collection of the sample from the discharge/bleed port.

The term "liquid" as used herein, in addition to the common usage of the term, also includes liquids which contain a solid phase, such as is the case with a mixture of oil, water and sand.

The term "vessel" as used herein refers to any sort of enclosure containing the liquid which is to be sampled. Thus, a vessel as so defined includes a pipe or other conduit through which the liquid flows as well as any container such as a process reactor which is holding the liquid to be sampled.

The term "clearance hole" as used herein refers to a hole which is sized such that the object which is referenced thereto is able to pass through or be contained in the hole without touching the walls of the hole.

The term "sample withdrawal" or related terminology as used herein refers to the process by which a sample of liquid is removed from a vessel and subsequently delivered to a desired sample location.

The term "compound actuator" as used herein refers to a pneumatic or hydraulic actuator (containing a primary piston and a cylinder) which also contains a secondary piston such that the primary and secondary pistons cooperate to effect the movement of the object being moved by the actuator.

BRIEF DESCRIPTION OF THE DRAWINGS

The drawings illustrate preferred embodiments which include the above-noted characteristics and features of the invention. The invention will be readily understood from the descriptions and drawings. In the drawings:

FIG. 10B is a cutaway perspective drawing of a seat for the ball valve of FIG. 9a.

DETAILED DESCRIPTION OF PREFERRED EMBODIMENTS

Figure 1:
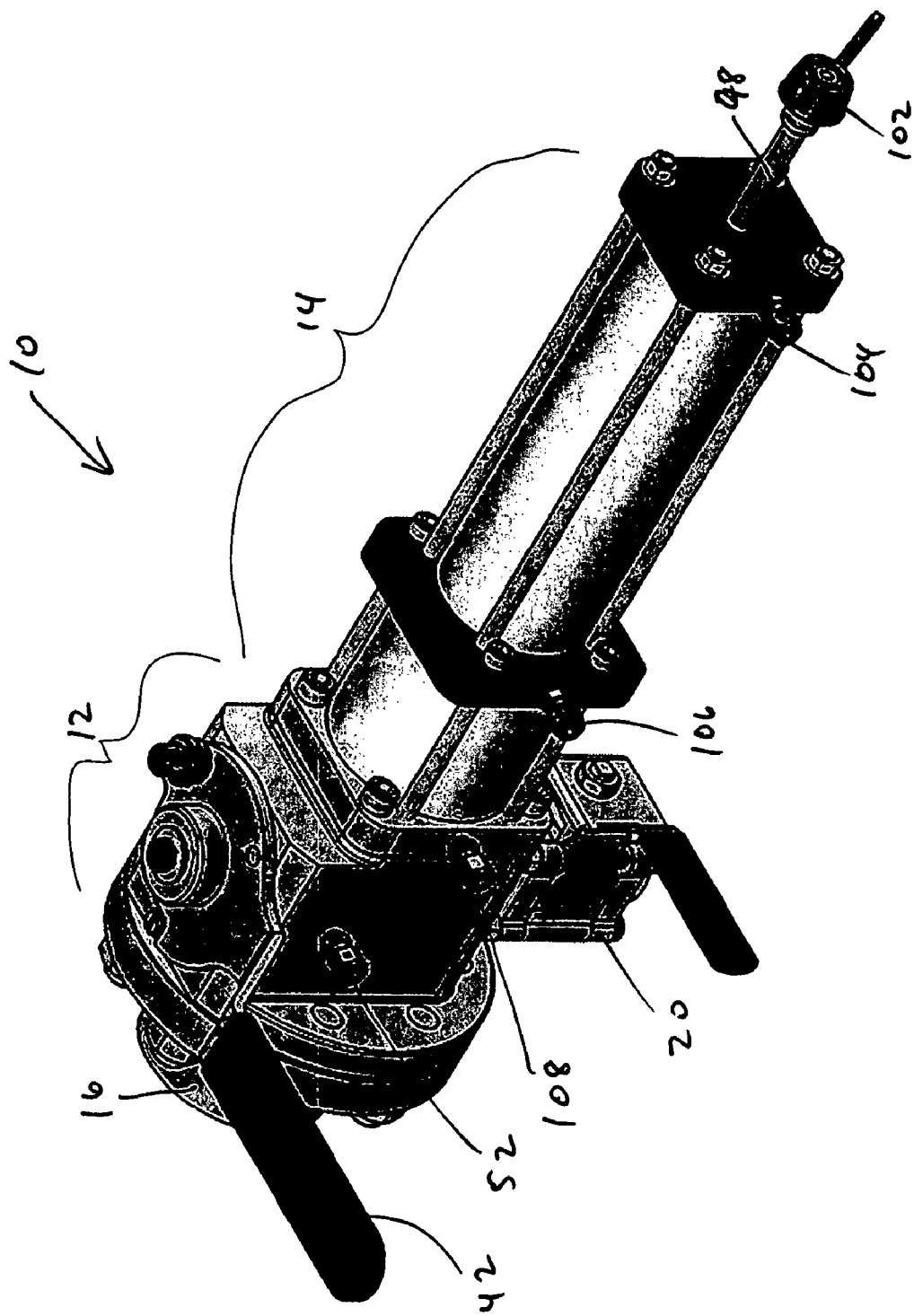
FIG. 1 is a perspective drawing of one embodiment of the inventive sampling apparatus.

FIG. 1 is a perspective drawing of sampling apparatus 10. FIGS. 2-5 and 7-9 are all cutaway perspective drawings of sampling apparatus 10 with the elements of apparatus 10 in different positions illustrating its operation. (To reduce the crowding of reference numbers, not all elements of sampling apparatus 10 are labeled in every figure.) Referring to FIGS. 1-5, sampling apparatus 10 has a valve portion 12 and an actuator portion 14. Sampling apparatus 10 is affixed by adapter 16 to a vessel 1 (shown in FIGS. 2-5) which contains the liquid (not shown) to be sampled through an adapter opening 18 (shown in FIGS. 2-5). Sampling apparatus 10 also includes a bleed valve 20 attached to valve portion 12 for the purpose of assisting in the collection of a sample taken by sampling apparatus 10.

Referring now to FIGS. 2-5 and FIGS. 8-9, valve portion 12 of sampling apparatus 10 includes valve 11 which has a valve body 22 containing a valve stem 24 and a central valve portion 26. Stem 24 is divided into two portions, a first stem portion 24a and a second stem portion 24b, by central valve portion 26, thus forming the stem and central valve portion of a trunnion valve. Central valve portion 26 is a spherical structure and has a through-hole 26h (best seen in FIGS. 5, 8 and 9) with an axis substantially perpendicular to the axis of stem 24; thus valve 11 in this embodiment is a ball valve. Through-hole 26h forms the sample-delivery site of sampling apparatus 10.

Figure 10A:
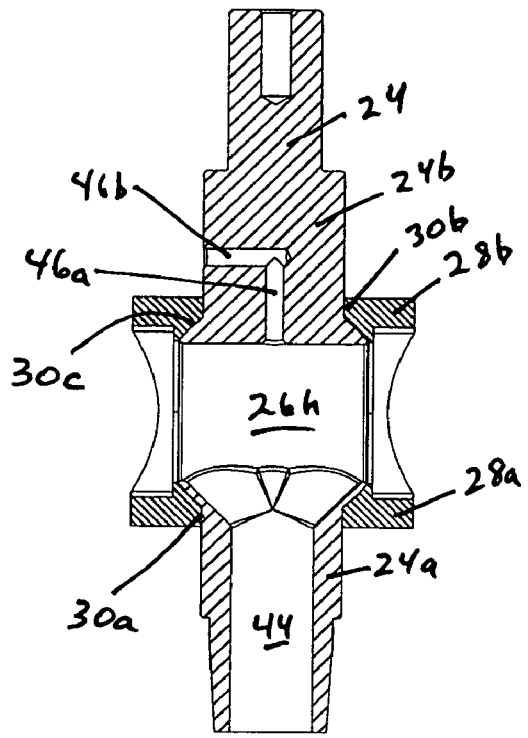
FIG. 10A is a cross-sectional drawing of the stem, central portion and the seat of a ball valve.
Figure 10C:
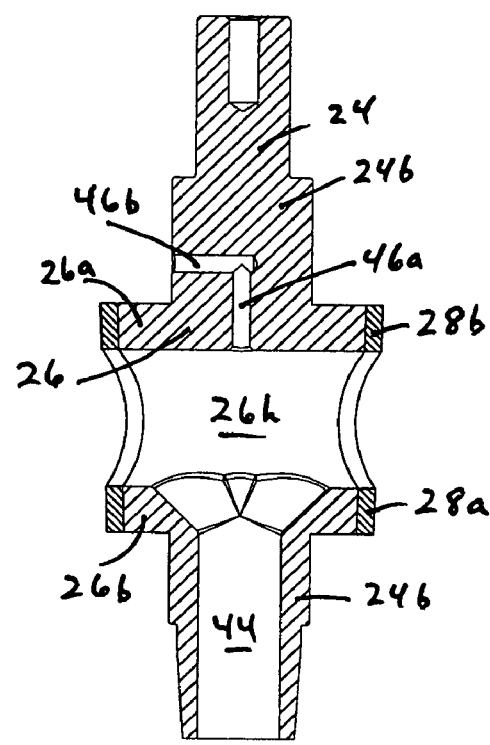
FIG. 10C is a cross-sectional drawing of the stem and central portion and the seat of a plug valve. The central portion is a truncated cone.
Figure 10B:
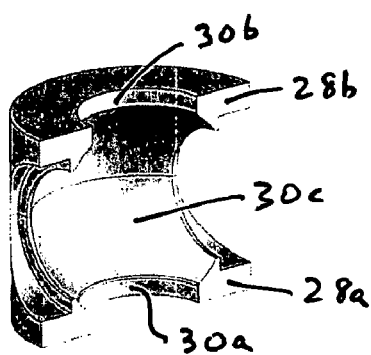

FIGS. 10A and 10B more clearly illustrate some of the details of stem 24 and central portion 26. Stem 24 and central portion 26 are surrounded, supported and sealed by a first valve seat 28a and a second valve seat 28b. First and second valve seats 28a and 28b engage first and second stem portions 28a and 28b respectively at first and second stem-engagement surfaces 30a and 30b and together engage central portion 26 at a central-portion-engagement surface 30c. First and second valve seats 28a and 28b thus ensure that stem 24 and central valve portion 26 remain in proper alignment within valve 11.

Figure 8:
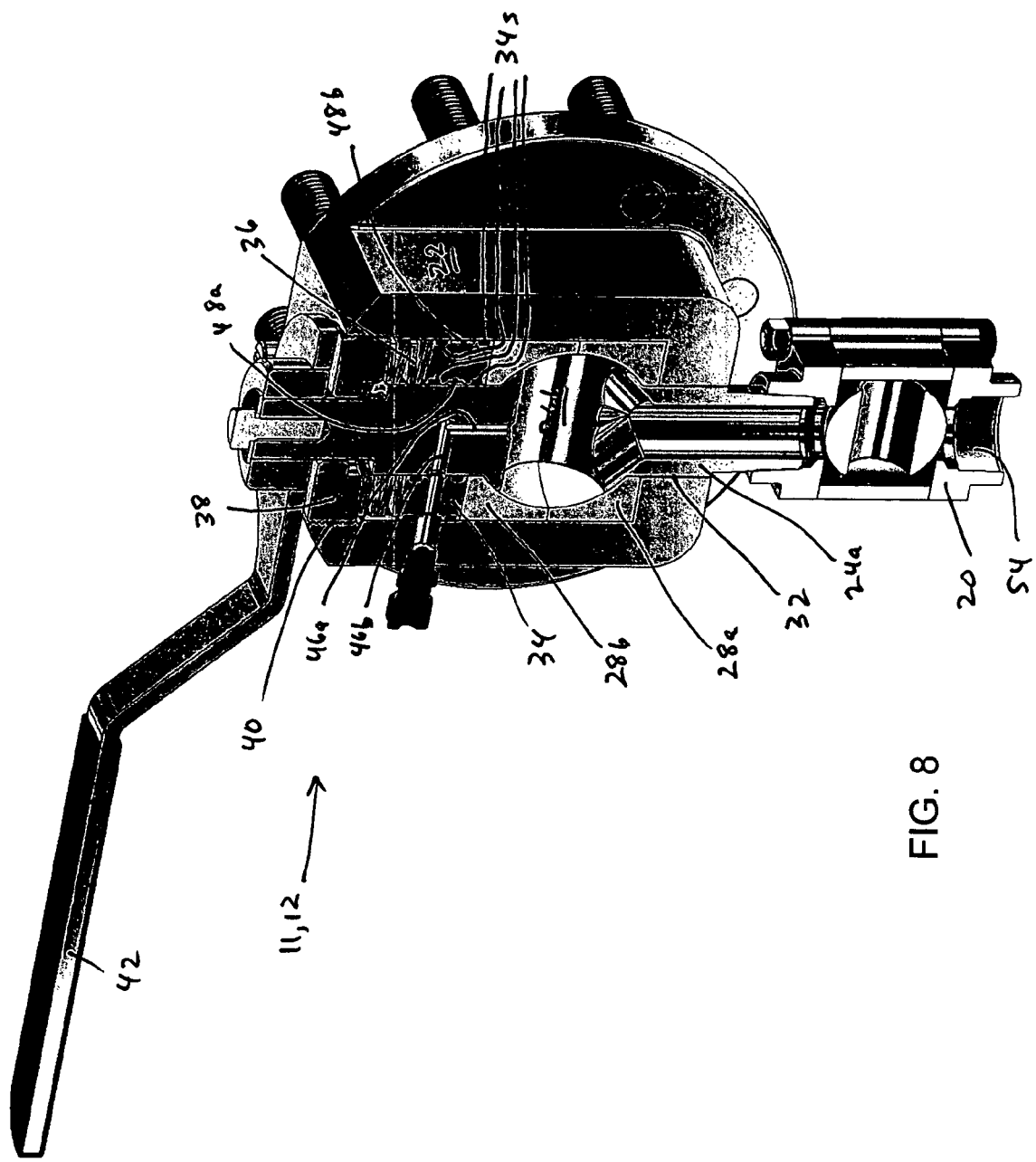
FIG. 8 is a cutaway perspective drawing of the valve of the sampling apparatus of FIG. 1, the plane of the cutaway being perpendicular to the cutaway plane of FIGS. 2-5. The valve is in a closed position, and the bleed valve is in a closed position.
Figure 9:
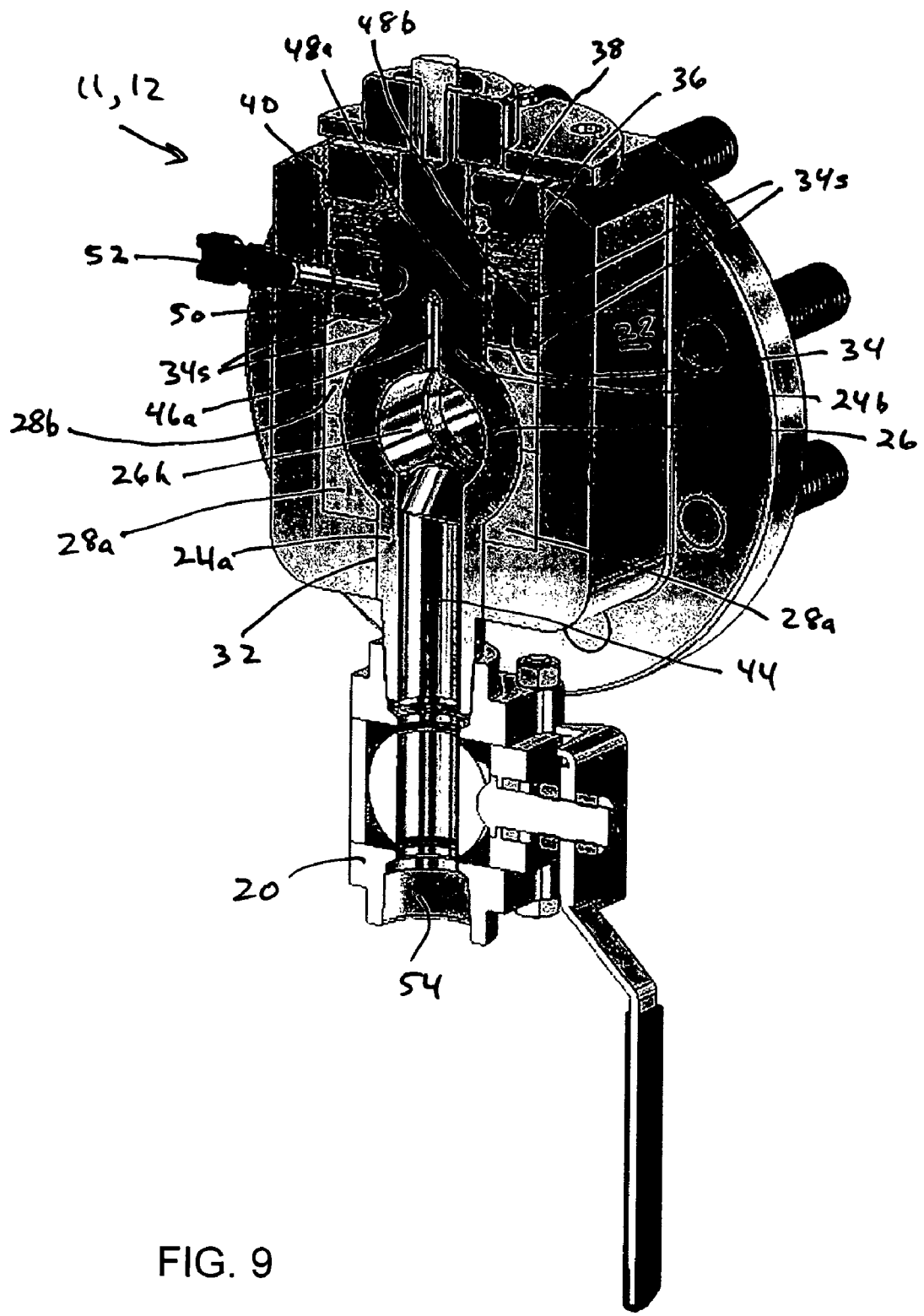
FIG. 9 is a cutaway perspective drawing of the valve of the sampling apparatus of FIG. 8 with the valve in an open position, and the bleed valve is in an open position.

Referring now to FIGS. 8 and 9 for further detail with respect to valve portion 12, first stem portion is partially supported by valve body 22 at a support surface 32 and by a set of gland seals 34s. Primary support for stem 24 and central portion is provided by seats 28a and 28b. First and second stem-engagement surfaces 30a and 30b thus form trunnion supports for first and second stem portions 24a and 24b within valve 11. Gland 34 is held in place by a bevel washer spring 36, and a packing bolt 38 is tightened into a threaded portion 40 of valve body 22 to complete the internal assembly of valve 11. Valve handle 42 is attached to stem 24 to effect turning of valve 11.

First stem portion 24a includes an axially-aligned sample discharge/bleed port 44. Port 44 is open to through-hole 26h, the sample-delivery site, thus enabling sample liquid to flow through first stem portion 24a into bleed valve 20 and, as desired, into a collection container (not shown) which may be connected to bleed valve sample port 54.

Second stem portion 24b includes a purge/flush inlet port 46. Port 46 includes axial passage 46a and intersecting passage 46b. Passage 46a is aligned axially with stem 24, and passage 46b intersects passage 46a in order to enable flow in port 46 to reach a pair of annular gland passages 48a and 48b which are connected together by a connecting passage 50. Annular gland passage 48b is aligned with an external flush port 52 (shown on FIGS. 1, 8 and 9). Thus, a flow passage exists in valve 11 between port 52 and through-hole 26h to effect purging and flushing of valve 11 regardless of the position of stem 24 of valve 11.

Figure 5:
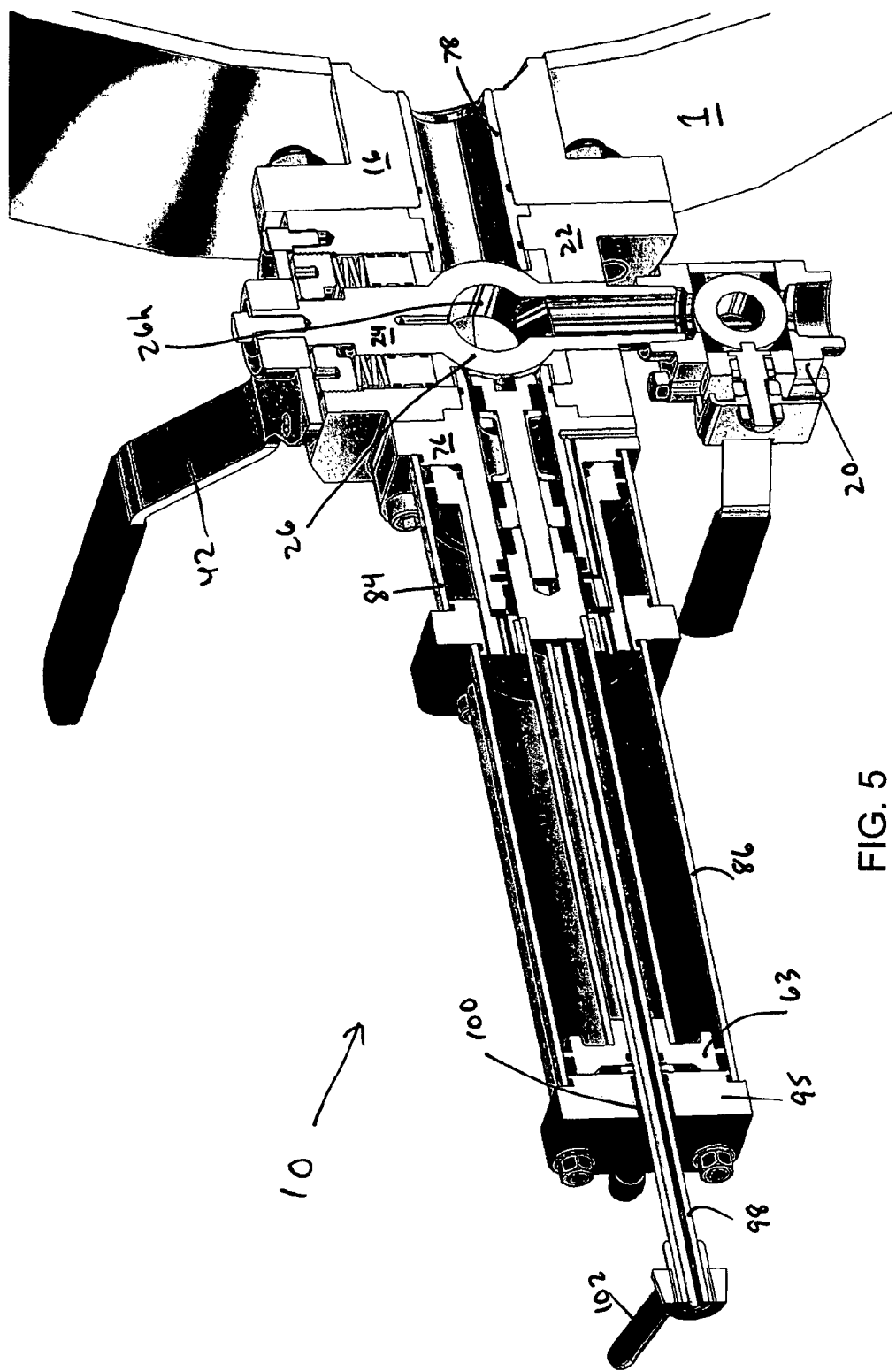
FIG. 5 is a cutaway perspective drawing of the sampling apparatus of FIG. 1 with the sample-receiving space beyond the sample-receiving site and with the ball valve in a closed position.
Figure 6:
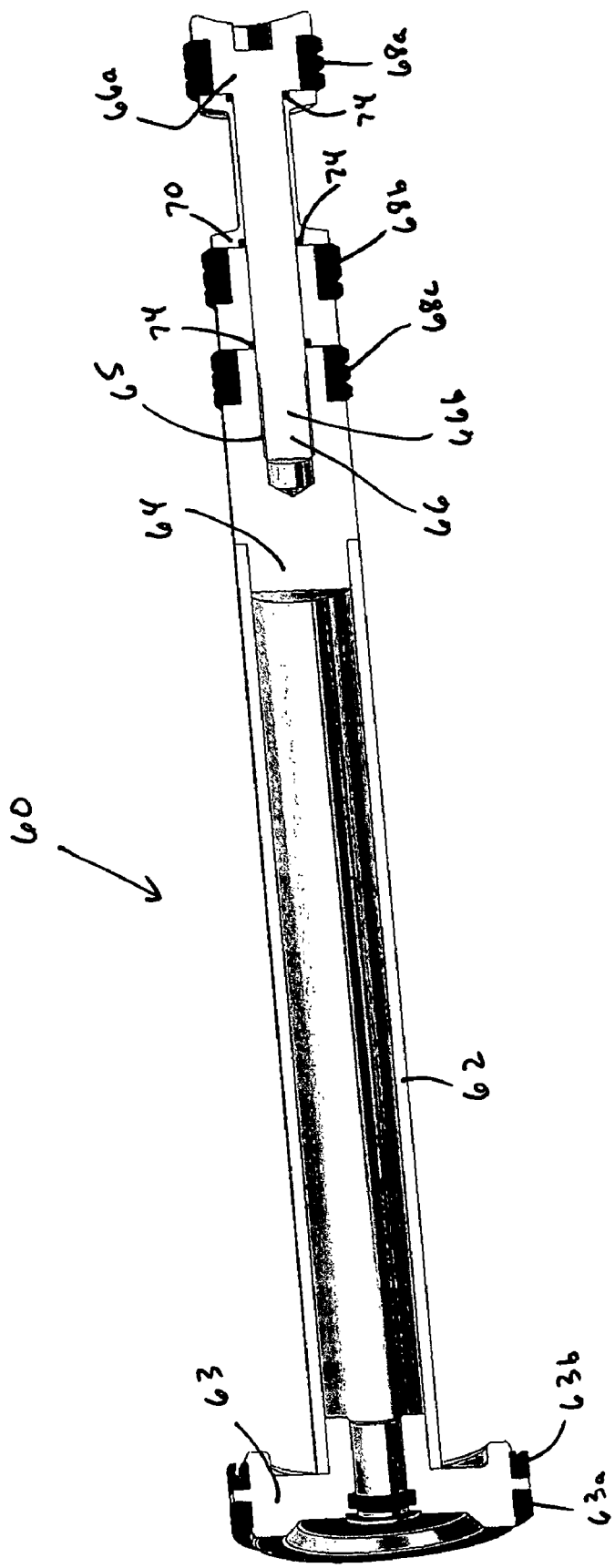
FIG. 6 is a cutaway perspective drawing of the plunger of the sampling apparatus of FIG. 1.
Figure 7:
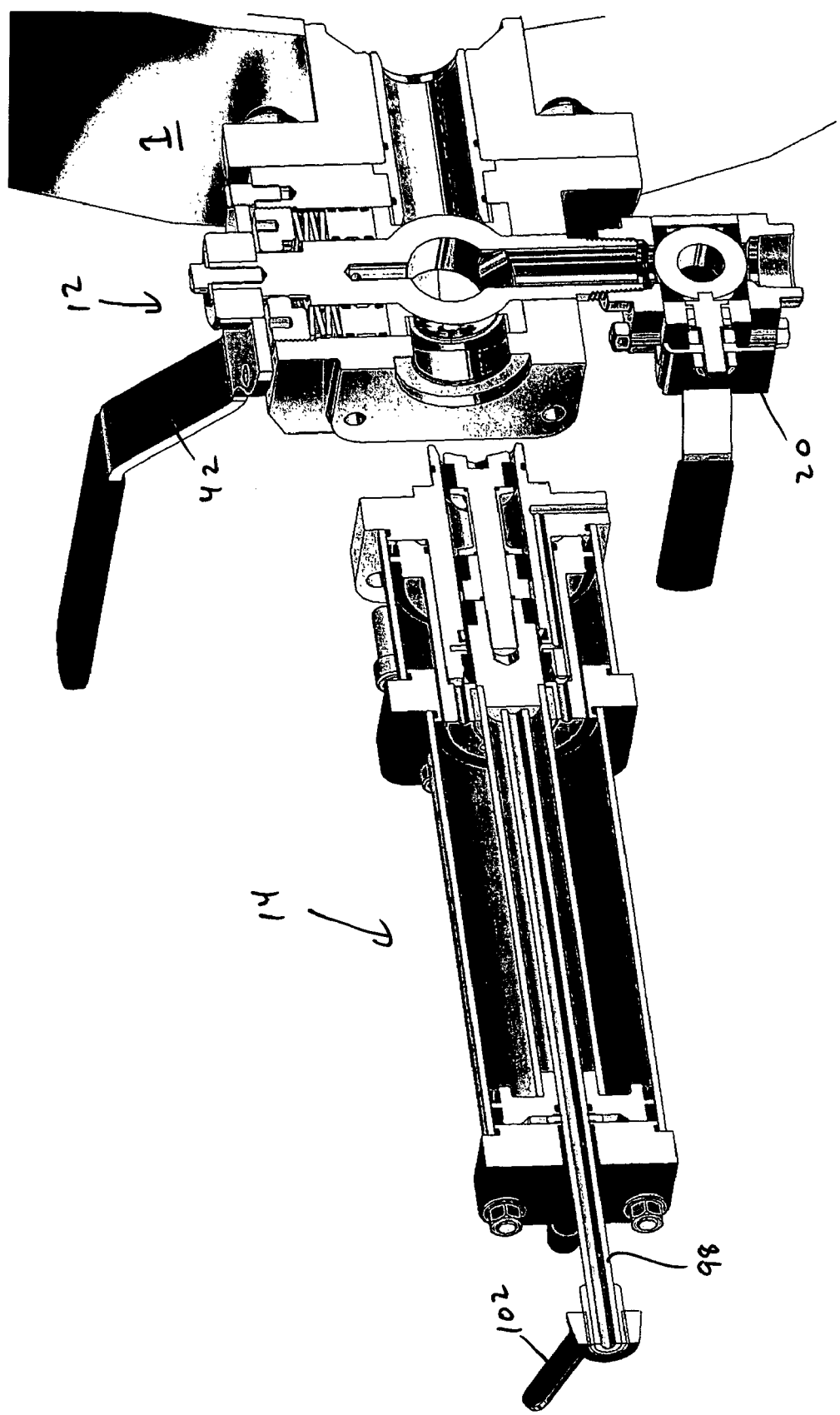
FIG. 7 is a cutaway perspective drawing of the sampling apparatus of FIG. 1 with the valve portion and the actuator portion separated for maintenance.

FIG. 6 is a cutaway perspective drawing of a plunger 60 of sampling apparatus 10. The various elements of plunger 60 can be seen in FIGS. 2-5 but are most easily seen in FIG. 6. Plunger 60 is assembled from a number of plunger elements. Plunger 60 includes a plunger tube 62 welded to plunger adapter 64 at one end of tube 62 and a rear piston 63 welded at the other end of tube 62. Adapter 64 includes a threaded hole 65 into which a mandrel 66 is inserted. Rear piston 63 includes rear piston seals 63a and 63b.

Mandrel 66 includes a mandrel head 66a and a mandrel shaft 66b. Onto mandrel 66 are assembled, in sequence, a front seal 68a, an O-ring 74 (all O-rings in this assembly are labeled with reference number 74 as similar elements), an annular spacer 70, an O-ring 74, a middle seal 68b, an O-ring 74, and a rear spacer 72. Annular spacer 70 forms the sample-receiving space of sampling apparatus 10. A rear seal 68c is placed onto plunger adapter 64, and mandrel 66 is inserted into threaded hole 65 in adapter 64, completing the assembly of plunger 60. Mandrel 66 is thus configured to enable easy disassembly and assembly to facilitate replacement of the seals on plunger 60.

Referring again to FIGS. 2-5, plunger 60 is slidably assembled into a rear sleeve 76 which is connected to valve body 22. Plunger 60 slides within sleeve 76, through through-hole 26h when stem 24 is in position to allow plunger 60 to enter hole through-hole 26h, and into and partially through a front sleeve 78 mounted in adapter 16 and body 22. O-rings 80 provide seals for plunger 60 within front sleeve 78 as shown. Rear sleeve 76 and front sleeve 78 form a pair of first and second axially-aligned plunger cylinders in which plunger 60 moves. The first plunger cylinder, front sleeve 78 is on the vessel side of valve 11, and the second plunger cylinder, rear sleeve 76, is on the opposite side of valve 11.

A front piston 82 is slidably assembled onto the outside of rear sleeve 76, into a front cylinder 84, and into a rear cylinder 86 such that front piston 82 slides within both front cylinder 84 and rear cylinder 86. Rear piston 63 of plunger 60 is also slidably assembled into rear cylinder 86. Front piston 82 includes a forward piston portion 82a and an aft piston portion 82b. Aft portion 82b includes a front piston sleeve bearing 88 in which plunger 60 slides, and rear sleeve 76 includes two rear sleeve seals 76a and 76b between which is an annular slot 92 connected to an intermediate drain/vent port 94 open to the outside of valve 11. The purpose of slot 92 and port 94 is that if seal 76a were to leak, liquid from sampling apparatus 10 would not find its way into rear cylinder 86 but rather simply flow through port 94 to the outside. Forward piston portion 82a includes two seals 85a and 85b for slidable support of front piston 82 within front cylinder 84.

Front cylinder 84 includes a center head 90 which forms the connection between front cylinder 84 and rear cylinder 86. Aft piston portion 82b includes an air passage 83 to allow air flow through aft piston portion 82b when front piston 82 is sliding with respect to rear sleeve 76.

Rear cylinder 86 includes a rear head 95 which closes off rear cylinder 86. Rear head 95 includes seals 96 which seal between rear head 95 and a stop tube 98 assembled into a threaded hole 100 in rear head 95 with a wing nut 102. Stop tube 98 functions to provide an air passage for displaced air when plunger 60 moves within rear cylinder 86. Stop tube 98 with a stop washer 99 mounted thereon also functions as a stop for plunger 60 as described below.

Front piston 82, front cylinder 84, rear piston 63 and rear cylinder 86, with their attendant seals, constitute a compound pneumatic actuator for effecting the movement of plunger 60 into the various positions required by sampling apparatus 10. Plunger 60 could be actuated by numerous other types of actuators including but not limited to simple pneumatic actuators, hydraulic actuators, and various electromechanical actuators.

FIGS. 2-5 illustrate four different positions of the plunger within sampling apparatus 60. These four positions constitute the specific positions which best describe the process of liquid sample withdrawal from vessel 1. Actuator portion 14 of sampling apparatus 10 moves plunger 60 to and from the various positions in order to effect sample withdrawal. FIG. 6 illustrates sampling apparatus 10 separated into valve portion 12 and actuator portion 14. In FIG. 6, wing nut 102 has been unscrewed to release stop tube 98, placing plunger 60 in a maintenance position. In this position, stop tube 98 can be used to push mandrel 66 out of rear sleeve 76, making it available for removal and replacement of seals 68a-68c as required or any other maintenance which may be required.

Figure 2:
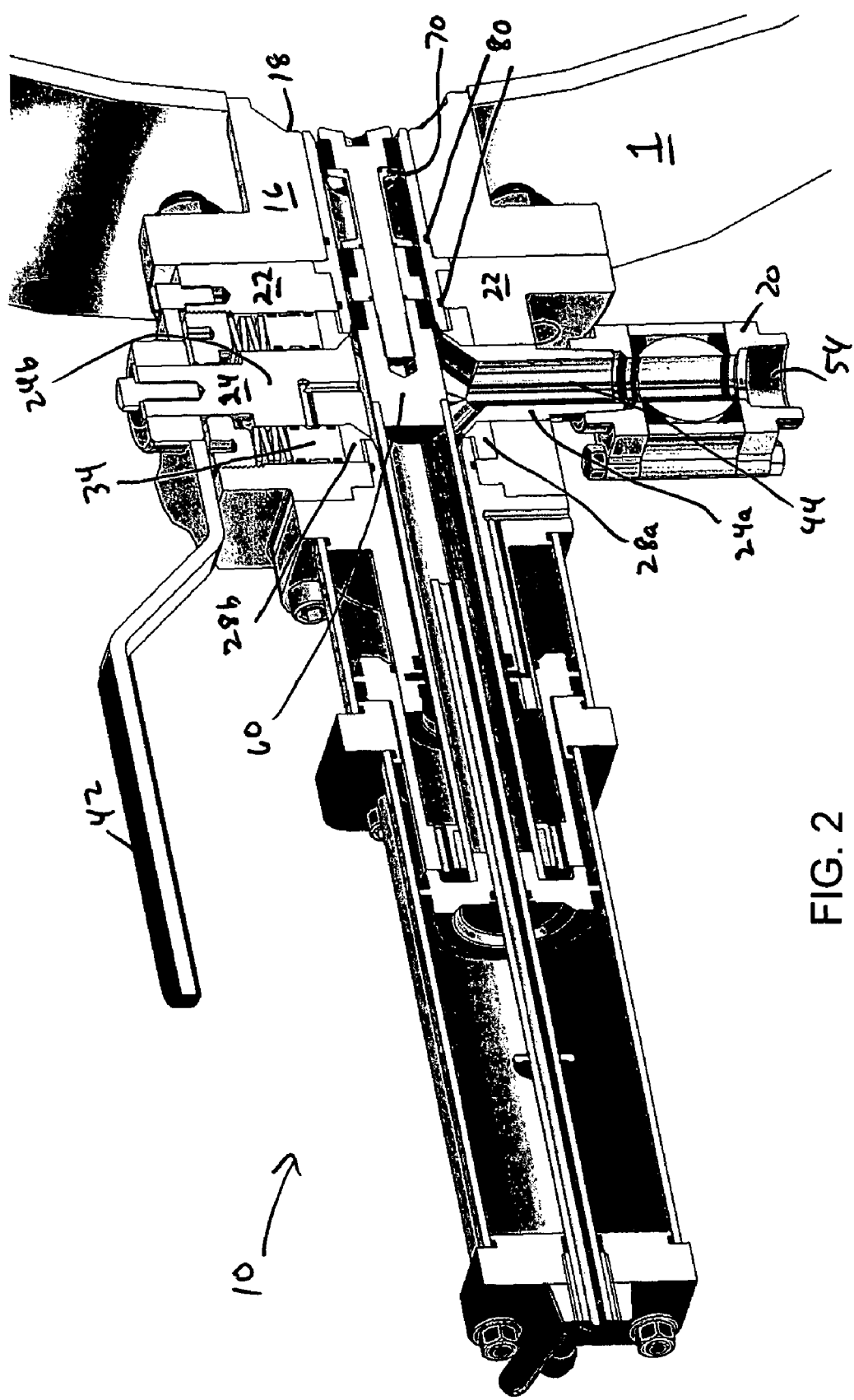
FIG. 2 is a cutaway perspective drawing of the sampling apparatus of FIG. 1 with the sample-receiving space between the vessel interior and the sample-delivery site and within the front sleeve.

FIG. 2 illustrates plunger 60 of sampling apparatus is the "parked" position, a position placing mandrel head 66a in a position to protect front sleeve 78 and mandrel head 66a from damage caused by abrasive liquid flowing in vessel 1. In this position, front piston 82 has been moved away from valve 11 to a position stopped by center head 90. To reach this position, actuator air is applied to a piston-park port 108 causing front piston 82 to move away from valve 11. Center head 90 provides a stopping position for front piston 82 which serves as a stop for rear piston 63.

Figure 3:
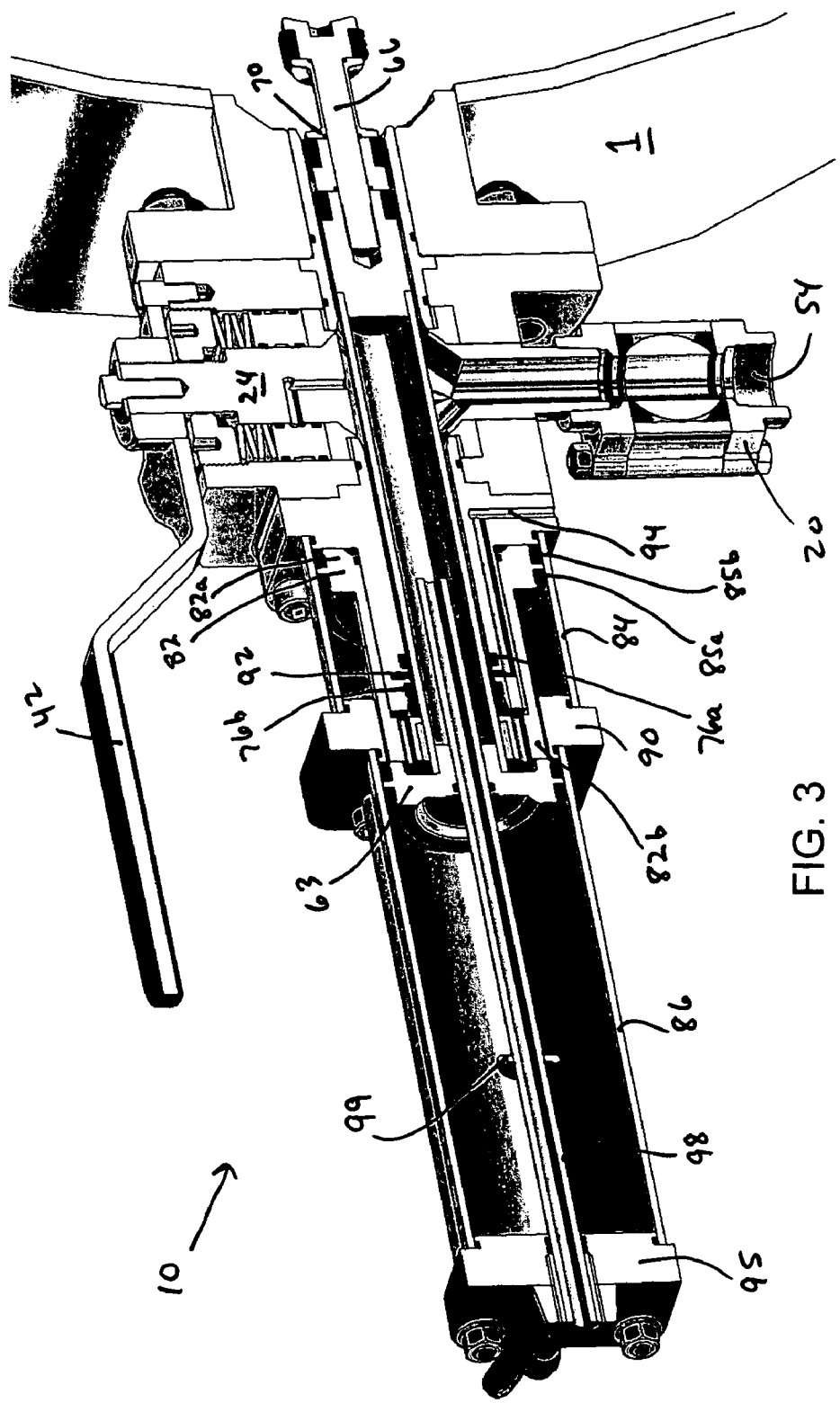
FIG. 3 is a cutaway perspective drawing of the sampling apparatus of FIG. 1 with the sample-receiving space in the vessel interior.

FIG. 3 illustrates plunger 60 of sampling apparatus 10 in position to receive a liquid sample from within vessel 1. Valve stem 24 is in position to align through-hole 26h such that plunger 60 may pass through central valve portion 26. In this sample-receiving position, the sample-receiving site formed within annular spacer 70 is open to capture liquid flowing through or being processed within vessel 1. In this position, both front piston 82 and rear piston 63 are positioned as close to valve 11 as possible within their respective cylinders. To reach this position, actuator air is applied to a piston-apply port 104 causing pistons 63 and 82 to move toward valve 11.

Figure 4:
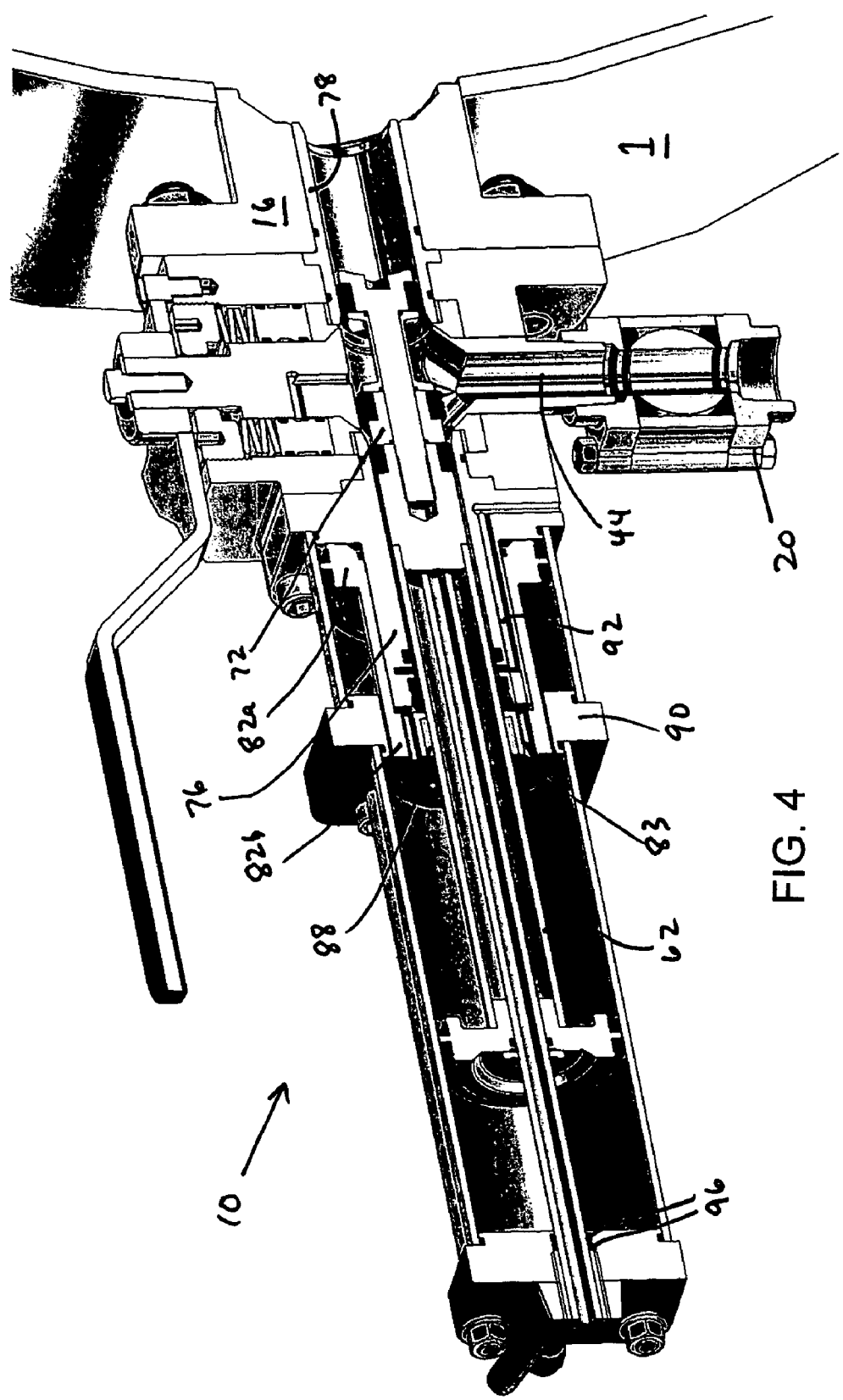
FIG. 4 is a cutaway perspective drawing of the sampling apparatus of FIG. 1 with the sample-receiving space at the sample-delivery site.

From the sample-receiving position, the fixed volume of liquid in the sample-receiving space is then moved through adapter opening 18 and through front sleeve 78 into through-hole 26h which forms the sample-delivery site. This sample-delivery position of sampling apparatus 10 is illustrated in FIG. 4. In the sample-delivery position, rear piston 63 is moved within rear cylinder 86 until it reaches stop washer 99 on stop tube 98. Stop washer 99 is positioned to place annular spacer 70 in the sample-delivery site within through-hole 26h in central valve portion 26. To reach this sample-delivery position, actuator air is applied to piston-retract port 106 to move rear piston 63 to its stop position created by stop washer 99.

In the sample-delivery position, bleed valve 20 can be used to effect transfer of the liquid sample contained in the sample-receiving space to a sample container (not shown) which may be connected to bleed valve 20 at bleed valve sample port 54. FIG. 8 illustrates bleed valve 20, a ball valve in this embodiment, in the closed position while sampling apparatus also in a closed position, indicating that sampling apparatus 10 is in a position ready for or undergoing maintenance as illustrated in FIGS. 5 and 6, respectively. FIG. 9 illustrates bleed valve 20 in an open position with valve 11 also in an open position, thereby allowing a liquid sample to pass from the sample-delivery site in through-hole 26h, through bleed valve 20 and into a sample container (not shown). Bleed valve 20 is attached to first stem portion 24a such that when valve 11 is turned using valve handle 42, the entire bleed valve 20 turns with stem 24.

FIG. 5 illustrates sampling apparatus in a maintenance position, ready for separation of actuator portion 14 from valve portion 12 as illustrated in FIG. 6. To reach this position, wing nut 102 is removed from rear head 95 thereby allowing stop tube to move stop washer 99 away from valve 11 and thus allowing plunger 60 to be removed from valve 11 completely. With the stop washer 99 back against rear head 95, actuator air applied to piston-retract port 106 causes rear piston to move farther back into rear cylinder 86.

A position called a "double-block-and-bleed" position is illustrated in FIG. 5. With sampling apparatus in a position ready for maintenance, an operator is able to use external flush port 52 in combination with bleed valve 20 to ensure that valve 11 has been properly closed, thus isolating vessel 1 from sampling apparatus 10, before sampling apparatus 10 is removed. In this position, it is also possible to ensure that the sample has been properly removed from the sample-delivery site in through-hole 26h. This position of sampling apparatus 10 thus provides safety for the operator during operation of sampling apparatus 10.

The selection of materials to be used for the embodiment described herein follows sound engineering practice as known by those skilled in the state-of-the-art of process monitoring, chemical instrument design or mechanical design. In general, parts within the embodiment described herein may be made of stainless steel such as 316SS but are not limited to being made of stainless steel. Seal materials for O-rings can be but are not limited to commercially-available O-ring materials such as Viton® or nitrile, both known to those skilled in the art of mechanical design.

Seals such as rear sleeve seals 76a and 76b may be made of PTFE (polytetrafluoroethylene) well known to those skilled in the art of mechanical design. Valve seats 28a and 28b may be made of TFM™, a modified PTFE material also well known to those skilled in the art of mechanical design. In some applications, front sleeve 78 may be required to withstand an highly-abrasive environment. In such cases, it may be useful to make front sleeve 78 from a material such as tungsten carbide. This and other materials are well-known to those skilled in the art of mechanical design. Front piston sleeve bearing 88 may be made of an appropriate sleeve bearing material such as silicon bronze or an oil- or PTFE-impregnated bearing material such as is well-known by those skilled in the art of mechanical design.

Front piston 82, front cylinder 84, rear piston 63, rear cylinder 86, center head 90, and rear head 95 all may be made out of aluminum.

None of material suggested herein are meant to be limiting to the scope of the present invention.

FIG. 10C illustrates an alternative embodiment for stem 24 and central valve portion 26. In FIG. 10C, central valve portion 26 is a truncated cone; a large end 26a of conical central valve portion 26 is adjacent to second stem portion 24b and a small end 26b of conical central valve portion 26 is adjacent to first stem portion 24a.

Referring to FIG. 3, when, for example, front seal 68a on mandrel head 66 of plunger 60 enters front sleeve 78 from vessel 1, seal 68a moves across a boundary between being unconstrained and being constrained (fitting tightly) within front sleeve 78. Such a transition is called a seal/interface encounter. Each such encounter is an opportunity for any abrasive solid phase in the liquid from vessel 1 that is carried by the seal to cause wear of the seals. One significant advantage of placing the sample-delivery site within valve 11 is that there are fewer such encounters during a sample withdrawal cycle than with sampling apparatus of the prior art such as that described in U.S. Pat. No. 6,792,818 mentioned above. If the sample-receiving space was moved to a sample-delivery site on the side of valve opposite to vessel 1 as in Jaeger '818, several additional wear-causing encounters would occur, thereby reducing the life of the seals as compared to those in the present invention. Furthermore, through-hole 26h is a clearance hole, i.e., larger in inside diameter compared to the outside diameters of front seal 68a, middle seal 68b, and rear seal 68c on mandrel 66 such that these seals do not touch the walls of through-hole 26h and such that any solid phase particles in the liquid being sample will not be pressed into these seals while sampling apparatus 10 is the sample-delivery position. In spite of the fact that first and second valve seats 28a and 28b ensure that stem 24 and central valve portion 26 remain in proper alignment within valve 11, through-hole 26h, being a clearance hole, also reduces the effect of any misalignment which may occur within valve 11 during the operation of sampling apparatus 10.

While the principles of this invention have been described in connection with specific embodiments, it should be understood clearly that these descriptions are made only by way of example and are not intended to limit the scope of the invention.

The invention claimed is:

1. In apparatus for withdrawing a liquid sample from a vessel, the apparatus affixed to the vessel and having (a) a plunger forming a sample-receiving space movable from the vessel interior to and beyond a sample-delivery site, and (b) a valve for closing the vessel when the plunger is beyond the sample-delivery site, the improvement comprising the sample-delivery site being incorporated in the valve.

2. The sampling apparatus of claim 1 wherein the valve is a trunnion valve.

3. The sampling apparatus of claim 2 wherein the valve has a stem and a central valve portion dividing the stem into a first stem portion and a second stem portion and having a through-hole with an axis substantially perpendicular to the stem axis.

4. The sampling apparatus of claim 3 wherein the first stem portion includes a discharge/bleed port aligned substantially along the axis of the stem for discharge of the sample from the sample-receiving space when such space is at the sample-delivery site.

5. The sampling apparatus of claim 4 wherein the plunger passes through the through-hole to (a) receive a sample from the vessel interior and (b) deliver the sample to the discharge/port.

6. The sampling apparatus of claim 5 wherein the through-hole is a clearance hole for the plunger.

7. The sampling apparatus of claim 3 wherein the second stem portion includes a purge/flush inlet port.

8. The sampling apparatus of claim 3 wherein the valve includes first and second valve seats that
   form stem-engagement surfaces for the first and second stem portions, respectively, and
   together form a central-portion-engagement surface, such that the first and second valve seats together surround, support, and seal the central valve portion and the first and second stem portions.

9. The sampling apparatus of claim 2 wherein the valve is a ball valve.

10. The sampling apparatus of claim 9 wherein the valve has a stem and a central valve portion dividing the stem into a first stem portion and a second stem portion and having a through-hole with an axis substantially perpendicular to the stem axis.

11. The sampling apparatus of claim 10 wherein the first stem portion includes a discharge/bleed port aligned substantially along the axis of the stem for discharge of the sample from the sample-receiving space when such space is at the sample-delivery site.

12. The sampling apparatus of claim 11 wherein the plunger passes through the through-hole to (a) receive a sample from the vessel interior and (b) deliver the sample to the discharge/port.

13. The sampling apparatus of claim 12 wherein the through-hole is a clearance hole for the plunger.

14. The sampling apparatus of claim 10 wherein the second stem portion includes a purge/flush inlet port.

15. The sampling apparatus of claim 10 wherein the valve includes first and second valve seats that
   form stem-engagement surfaces for the first and second stem portions, respectively, and
   together form a central-portion-engagement surface, such that the first and second valve seats together surround, support, and seal the central valve portion and the first and second stem portions.

16. The sampling apparatus of claim 2 wherein the valve is a plug valve.

17. The sampling apparatus of claim 1 wherein:
   the plunger moves within first and second axially-aligned plunger cylinders, the first on the vessel side of the valve and the second on the opposite side of the valve;
   the sample-receiving space is an annular space; and
   the plunger includes first and second plunger seals each mounted beyond a respective end of the sample-receiving space and spaced such that when the sample-receiving space is at the sample-delivery site, the first and second plunger seals are engaging the first and second plunger cylinders, respectively.

18. The sampling apparatus of claim 1 further including a compound actuator for plunger movement.

19. The sampling apparatus of claim 1 further including a bleed valve to effect collection of the sample from the discharge/bleed port.

* * * * *

UNITED STATES PATENT AND TRADEMARK OFFICE
CERTIFICATE OF CORRECTION

PATENT NO.         : 7,481,124 B2
APPLICATION NO. : 11/439585
DATED              : January 27, 2009
INVENTOR(S)        : Schadt It is certified that error appears in the above-identified patent and that said Letters Patent is hereby corrected as shown below:

In column 5, line 2, delete "9a" and insert --10A--.

In column 8, line 43, delete "an" and insert --a--.

In column 10, claim 19, line 52, delete "1" and insert --4--.

Signed and Sealed this

Fourth Day of August, 2009

JOHN DOLL
*Acting Director of the United States Patent and Trademark Office*